US011487028B2

United States Patent
Verhaegen et al.

(10) Patent No.: US 11,487,028 B2
(45) Date of Patent: Nov. 1, 2022

(54) DEVICE FOR SUPPORTING THE TESTING OF A BRACHYTHERAPY APPLICATOR AND A METHOD FOR TESTING OF SUCH A BRACHYTHERAPY APPLICATOR PRIOR TO THE USE OF THE BRACHYTHERAPY APPLICATOR IN BRACHYTHERAPY RADIATION TREATMENTS

(71) Applicants: Universiteit Maastricht, Maastricht (NL); Stichting Maastricht Radiation Oncology "Maastro-Clinic", Maastricht (NL); Academisch Ziekenhuis Maastricht, Maastricht (NL)

(72) Inventors: Frank Verhaegen, Maastricht (NL); Gabriel Paiva Fonseca, Maastricht (NL); Robert Voncken, Maastricht (NL)

(73) Assignees: UNIVERSITET MAASTRICHT, Maastricht (NL); STICHTING MAASTRICHT RADIATION ONCOLOGY "MAASTRO-CLINIC", Maastricht (NL); ACADEMISCH ZIEKENHUIS MAASTRICHT, Maastricht (NL)

( * ) Notice: Subject to any disclaimer, the term of this patent is extended or adjusted under 35 U.S.C. 154(b) by 357 days.

(21) Appl. No.: 16/498,604

(22) PCT Filed: Mar. 21, 2018

(86) PCT No.: PCT/EP2018/057172
§ 371 (c)(1),
(2) Date: Sep. 27, 2019

(87) PCT Pub. No.: WO2018/177842
PCT Pub. Date: Oct. 4, 2018

(65) Prior Publication Data
US 2021/0109239 A1 Apr. 15, 2021

(30) Foreign Application Priority Data

Mar. 27, 2017 (EP) .................................... 17163112

(51) Int. Cl.
*A61N 5/10* (2006.01)
*G01T 1/29* (2006.01)
*G06T 7/60* (2017.01)

(52) U.S. Cl.
CPC ................ *G01T 1/29* (2013.01); *A61N 5/103* (2013.01); *A61N 5/1007* (2013.01); *G06T 7/60* (2013.01); *A61N 2005/1008* (2013.01)

(58) Field of Classification Search
CPC ........ A61N 5/1001–1029; A61N 5/103; A61N 5/1075; G01T 1/29; G06T 7/60
See application file for complete search history.

(56) References Cited

U.S. PATENT DOCUMENTS 5,561,698 A 10/1996 Mick
2013/0303902 A1 11/2013 Smith
(Continued)

OTHER PUBLICATIONS

Awunor et al., "A multicenter study to quantify systematic variations and associated uncertainties in source positioning with commonly used HDR afterloaders and ring applicators for the treatment of cervical carcinomas," Int. J. Med. Phys. Research and Practice, vol. 42 No. 8, p. 4472-4483, Aug. 2015. (Year: 2015).*
(Continued)

*Primary Examiner* — Thaddeus B Cox
(74) *Attorney, Agent, or Firm* — Nixon Peabody LLP

(57) ABSTRACT

The invention relates to a device for supporting the testing of a brachytherapy applicator prior to the use of the brachytherapy applicator in brachytherapy radiation treatments.

(Continued)

The invention also relates to a method for testing of a brachytherapy applicator prior to the use of the brachytherapy applicator in brachytherapy radiation treatments.

10 Claims, 13 Drawing Sheets

(56) References Cited

U.S. PATENT DOCUMENTS

2016/0325120 A1 11/2016 Cernica
2019/0051424 A1* 2/2019 Muehlhauser ......... G21K 1/025

OTHER PUBLICATIONS

International Search Report for International Application No. PCT/EP2018/057172, dated Jun. 4, 2018 (4 pages).
Written Opinion of International Searching Authority for International Application No. PCT/EP2018/057172, dated Jun. 4, 2018 (5 pages).

* cited by examiner though DEVICE FOR SUPPORTING THE TESTING OF A BRACHYTHERAPY APPLICATOR AND A METHOD FOR TESTING OF SUCH A BRACHYTHERAPY APPLICATOR PRIOR TO THE USE OF THE BRACHYTHERAPY APPLICATOR IN BRACHYTHERAPY RADIATION TREATMENTS

CROSS-REFERENCE TO RELATED APPLICATIONS

This application is a national stage of Application No. PCT/EP2018/057172 filed Mar. 21, 2018, and claims the benefit of priority from European Application number 17163112.0 filed on Mar. 27, 2017, which are both incorporated by reference in their entireties.

FIELD OF THE INVENTION

The invention relates to a device for supporting the testing of a brachytherapy applicator prior to the use of the brachytherapy applicator in brachytherapy radiation treatments.

The invention also relates to a method for testing of a brachytherapy applicator prior to the use of the brachytherapy applicator in brachytherapy radiation treatments.

The invention furthermore relates to a radiation therapy treatment planning system for use in effecting radiation therapy of a pre-selected anatomical portion of a human or animal body cooperating with a device according to the invention.

BACKGROUND OF THE INVENTION

Brachytherapy radiation therapy relates to the placement of radioactive sources inside an anatomical portion of a human and/or animal body (the patient) on a temporary or permanent basis. The radiation being emitted causes damage to the cancer cells' DNA and destroys their ability to divide and grow further. A brachytherapy technique involves internally applied radiation beams, by employing an applicator that allows a radioactive source (High Dose Rate or Pulsed Dose Rate source) to be introduced, and positioned near or at the tumor site. An example of a HDR radioactive source is $^{192}$Ir.

Such brachytherapy applicator can be embodied in many configurations. In general many applicator configurations are based on an applicator design capable of insertion in an anatomical cavity of the human or animal body near the tumor site, as well as at least one applicator channel through which a radiation emitting source can be guided and positioned at several, distinct dwell positions near or at the tumor site.

The commissioning of a brachytherapy applicator of a certain configuration prior to clinical use is essential to verify conformance with the manufacturer's specifications assuring the correct delivery of radiation towards the tumor site during brachytherapy radiation treatment and also to ascertain patient safety. The testing process may include mechanical inspection, offset measurements, verification of the dwell positions and dose measurements. Most of the measurements are currently performed using radiochromic films, that can provide high 2D spatial accuracy and near-instantaneous response.

Although test measurements implementing radiochromic films can be accurate, the time necessary to perform several test measurements can be significant since a new film should be positioned before each test experiment, which also increases the test uncertainty. Therefore, the time to align the subsequent films, to process the results and also the cost of the films limit the number of measurements for testing the brachytherapy prior to its actual clinical use in a brachytherapy radiation treatment.

In addition, during the test measurements using film it is not possible to verify short interdwell distances (≤0.5 cm using single measurements) commonly employed in the dose planning stage prior to the treatment and executed during the actual radiation treatment. This is because during the testing of the subsequent dwell positions the radiochromic film is exposed to radiation for a prolonged period of time, resulting in a partial overlap and hence in a blurry or distorted image. In particular the integrated response of the film is not sufficient to visually distinguish between the separate independent, dwell positions during the test.

In addition, during the test measurements using film it is not possible to derive any timing information on the dwell times. This is because the film integrates all signals over time and cannot provide time-resolved information. Verification of dwell times is an essential part of verifying a treatment plan.

DESCRIPTION OF THE INVENTION

The invention aims to provide a solution for the above identified problems, and therefore a device for supporting the testing of a brachytherapy applicator prior to the use of the brachytherapy applicator in high dose rate or pulsed dose rate brachytherapy radiation treatments is proposed, said device comprising a radiation capturing screen, an imaging holder positioned at a distance from the radiation capturing screen and being arranged for accommodating a radiation emitting source, an applicator test holder positioned between the imaging holder and the radiation capturing screen, the applicator test holder being arranged for holding the brachytherapy applicator, wherein the radiation capturing screen is arranged in capturing radiation being emitted by said radiation emitting source in subsequent, independent images.

Herewith a proper image for visualizing and quantifying the brachytherapy applicator can be obtained, based on which visualizing and quantifying it can be ascertained whether said brachytherapy applicator can be properly used in high dose rate or pulsed dose rate brachytherapy radiation treatments.

In an example said imaging holder comprises a channel for accommodating the radiation emitting source and furthermore the device comprises radiation emitting source drive means for driving said radiation emitting source through said imaging holder, wherein said radiation emitting source drive means are further arranged for driving said radiation emitting source through said brachytherapy applicator, being held by said applicator test holder. In a further example said radiation emitting source drive means are connected to an afterloading apparatus. This allows the device according to the invention to be coupled with a known afterloading apparatus already installed in a hospital for testing the brachytherapy applicators prior to the use of said applicators in brachytherapy treatments to be performed with said afterloading apparatus In yet a further example the device comprises image processing means for visualizing and quantifying the geometrical dimensions of said brachytherapy applicator based on processing the subsequent, independent images being captured. In particular the image processing means are arranged for correcting the subsequent, independent images for background exposure signals, which will improve the visualization of the brachytherapy application under test and reduce diagnosis errors as to the suitability of the applicator for use in subsequent brachytherapy radiation treatments to be performed.

In yet a further example the image processing means are arranged to generate applicator dimension data relating to the reconstructed geometrical dimensions of said brachytherapy applicator, said applicator dimension data being suitable for use in a radiation treatment planning system for effecting radiation brachytherapy therapy in a pre-selected anatomical portion of a human or animal body using said brachytherapy applicator being tested. Herewith a rejection of a brachytherapy applicator as being not conformal to the original designer's specifications is avoided, as the tested brachytherapy applicator can still be used in performing brachytherapy radiation treatments as the radiation treatment planning system is now capable in generating radiation treatment plans using the correct applicator dimension data being obtained during the test procedure steps according to the invention.

Furthermore the device comprises a support plate containing the radiation capturing screen, wherein the support plate is provided with multiple position markers. These markers will become visible in the subsequent independent images obtained and assist in the diagnosis by the testing personnel.

The method for testing of a brachytherapy applicator prior to the use of the brachytherapy applicator in high dose rate or pulse dose rate brachytherapy radiation treatments using the test supporting device according to the invention comprises the steps of c) positioning a brachytherapy applicator to be tested in the applicator test holder of the device; d) positioning a radiation emitting source in the imaging holder of the device; e) capturing radiation being emitted by said radiation emitting source with said radiation capturing screen in subsequent, independent images of a first type; f) positioning the radiation emitting source in the brachytherapy applicator to be tested and being held in the applicator test holder; g) capturing radiation being emitted by said radiation emitting source with said radiation capturing screen in subsequent, independent images of a second type; and h) visualizing and quantifying the geometrical dimensions of said brachytherapy applicator based on processing the subsequent, independent images of the first and second type being captured.

In particular step f) comprises the step of f-1) positioning the radiation emitting source for certain dwell times at one or more dwell positions in the brachytherapy applicator. In addition step c) is preceded by the steps of a) positioning the radiation emitting source in the imaging holder of the device with no brachytherapy applicator to be tested being held in the applicator test holder; b) capturing radiation being emitted by said radiation emitting source with said radiation capturing screen in subsequent, independent images of an initial type. Furthermore step h) comprises the step of h-1) correcting the subsequent, independent images of the first and second type for background exposure signals using the subsequent, independent images of the initial type. In particular step h-1) involves the step h-2) of substracting the subsequent, independent images of the initial type from the subsequent, independent images of the first and second type, thereby creating a clear representation of the brachytherapy applicator in the images.

Herewith all irrelevant image information can be eliminated in the images and only the relevant image information is made visible thereby improving the analysis thereof and the subsequent visualization and quantification of the brachytherapy applicator under test.

In addition the method may comprise the steps of i-1) determining the positions of the radiation emitting source in at least three subsequent, independent images being captured during step f-1); i-2) deciding whether said positions are within a predefined distance range; and i-3) when it has been decided that said positions are within said predefined distance range, identifying that the radiation emitting source is positioned at a dwell position within the brachytherapy applicator. As such the brachytherapy applicator can also be tested under the treatment conditions where a radiation emitting source is to be advanced at subsequent distinct dwell positions which are located at a small interdwell distance from each other.

With the prior art technique using radiochromic films short interdwell distances ($\leq 0.5$ cm using single measurements), which are commonly employed in the doses planning stage prior to the treatment and executed during the actual radiation treatment cannot be verified or determined because when the film is exposed to radiation for a prolonged period of time, this results in a partial overlap of the adjacent dwell positions of the radiation emitting source and hence in a blurry image the blurring of the film being due to the overlap of the signals of the individual dwell positions.

In a further example of the method it also comprises the step i-4) verifying that the radiation emitting source remains at the dwell position being identified for a predefined dwell time.

In a further example, the method comprises the steps of j-1) generating applicator dimension data relating to the reconstructed geometrical dimensions of said brachytherapy applicator; j-2) inputting said applicator dimension data in a radiation treatment planning system. Herewith a rejection of a brachytherapy applicator as being not conformal to the original designer's specifications is avoided, as the tested brachytherapy applicator can still be used in performing brachytherapy radiation treatments as the radiation treatment planning system is now capable in generating radiation treatment plans using the correct applicator dimension data being obtained during the test procedure steps according to the invention.

The invention also relates to an assembly for testing a brachytherapy applicator prior to the use of said brachytherapy applicator in high dose rate or pulsed dose rate brachytherapy radiation treatments, said assembly being composed of a device according to the invention, as well as a brachytherapy afterloading apparatus comprising radiation emitting source drive means being connected to said testing device according to the invention.

The invention also relates to a radiation therapy treatment planning system for use in effecting radiation therapy of a pre-selected anatomical portion of a human or animal body, wherein a brachytherapy applicator inserted in a certain orientation into said anatomical portion, said brachytherapy applicator being identified in said radiation therapy treatment planning system by means of applicator dimension data, said applicator dimension data defining at least one trajectory for at least one radiation emitting source to be displaced along said trajectory through said brachytherapy applicator, said radiation treatment planning system comprising treatment planning means for generating a radiation treatment plan for effecting said radiation therapy, said treatment plan at least comprising said applicator dimension data concerning the number, the position and the direction of said at least one trajectory of said brachytherapy applicator within said anatomical portion to be treated, default dwell step, dwell positions and dwell times for said at least one radiation emitting source along said at least one trajectory, and a radiation dose distribution for each of said at least one trajectory, and wherein said treatment planning means are arranged in receiving and using applicator dimension data being obtained from a brachytherapy applicator being tested with the device according to the invention or the method according to the invention.

BRIEF DESCRIPTION OF THE DRAWINGS

The invention will now be described in more detail with reference to the accompanying drawings, which drawings show in:

FIG. 5a an image obtained with the device in the initial test condition shown in FIG. 4a;

FIG. 5b an image obtained with the device in the first test condition shown in FIG. 4b;

FIG. 5c an image obtained with the device in the first test condition shown in FIG. 4b and corrected for background exposure with the image of FIG. 5a;

FIG. 5d the image of FIG. 5c corrected for projected distortion according to the correction process as shown in FIG. 7;

DETAILED DESCRIPTION OF THE INVENTION

Figure 1A:
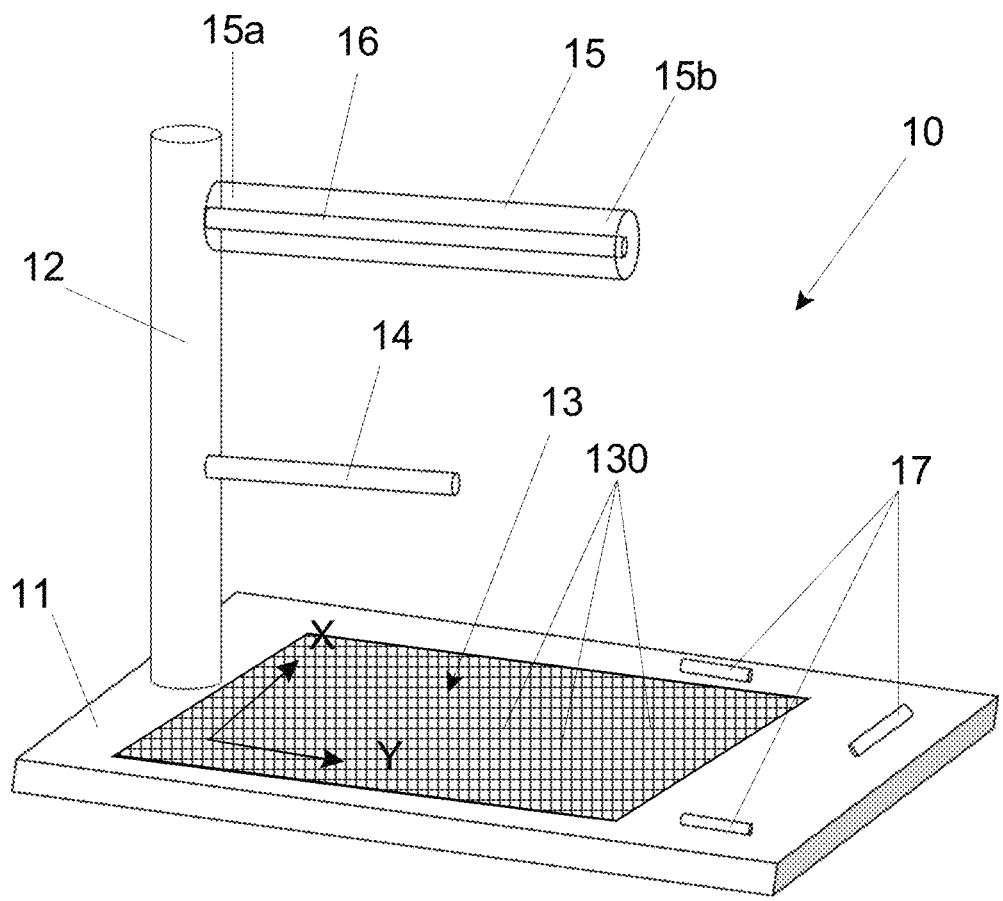
FIGS. 1a and 1b embodiments of a test supporting device according to the invention.

For a better understanding of the invention like parts in the drawings are to be denoted with like reference numerals.

Figure 1B:
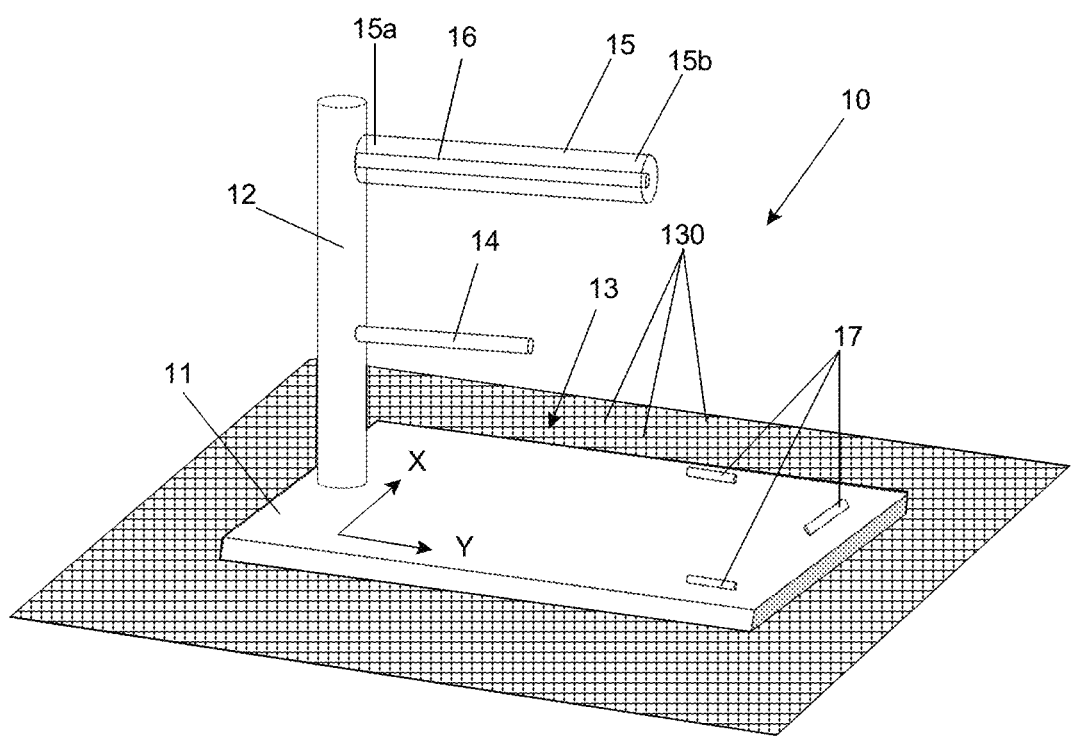

FIGS. 1a and 1b disclose two embodiments of device for supporting the testing of a brachytherapy applicator prior to the use of said brachytherapy applicator in high dose rate or pulsed dose rate brachytherapy radiation treatment. In FIGS. 1a and 1b the test supporting device is denoted with reference numeral 10 and is predominantly composed of radiation capturing screen 13, an imaging holder 15 which is positioned at some distance from the radiation capturing screen 13. The imaging holder 15 is arranged for accommodating during use a radiation emitting source.

Furthermore, the test supporting device 10 comprises an applicator test holder 14, which applicator test holder 14 is positioned between imaging holder 15 and the radiation capturing screen 13.

In particular, the test support device 10 is composed of a construction frame built up from a support plate 11 and a support stand 12, which is mounted on the support plate 11. The support stand 12 also supports the applicator test holder 14 and the imaging holder 15. In the embodiments of FIGS. 1a and 1b both the applicator test holder 14 and the imaging holder 15 are constructed as elongated support bars or shafts. The applicator test holder 14 is arranged in supporting or holding a brachytherapy applicator to be tested using specific, known clamping elements.

As depicted in FIG. 1a, the radiation capturing screen 13 is accommodated in the support plate 11, whereas in the embodiment shown in FIG. 1b the radiation capturing screen 13 is positioned under the support plate 11.

The support plate 11 is furthermore provided with position markers 17, which in an example are made from a radio opaque material allowing the markers 17 to be made visible in the images which are captured with the radiation capturing screen during testing. The position markers 17 can also be constructed as fiducial markers.

The imaging holder 15 is provided with an imaging holder channel 16, which is provided as a bore running through the elongated shaft-like imaging holder 15 from the proximal imaging holder end 15a till the free, distal imaging holder end 15b.

As outlined further in the figurative description the imaging holder channel or bore 16 functions to accommodate a radiation emitting source which will be guided and positioned through the imaging holder channel 16, using suitable radiation emitting source drive means.

Figure 4A:
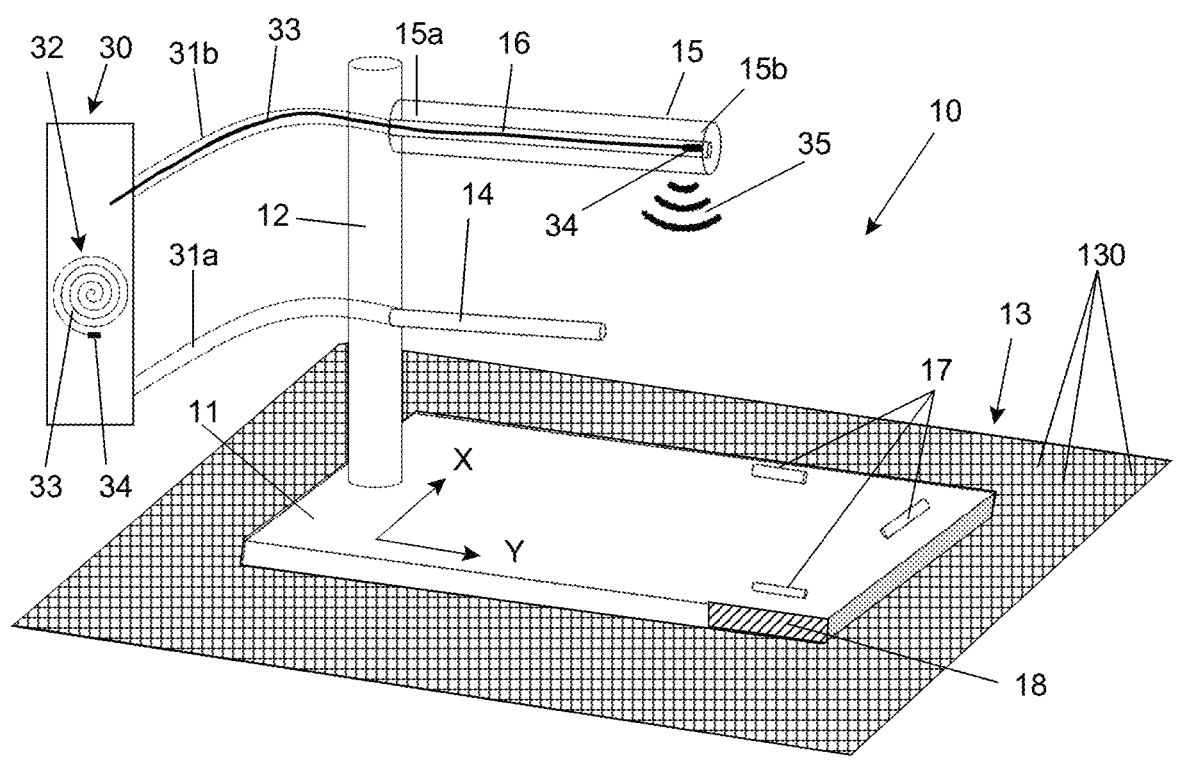
FIG. 4a the device of FIG. 1b in an initial test condition.
Figure 4B:
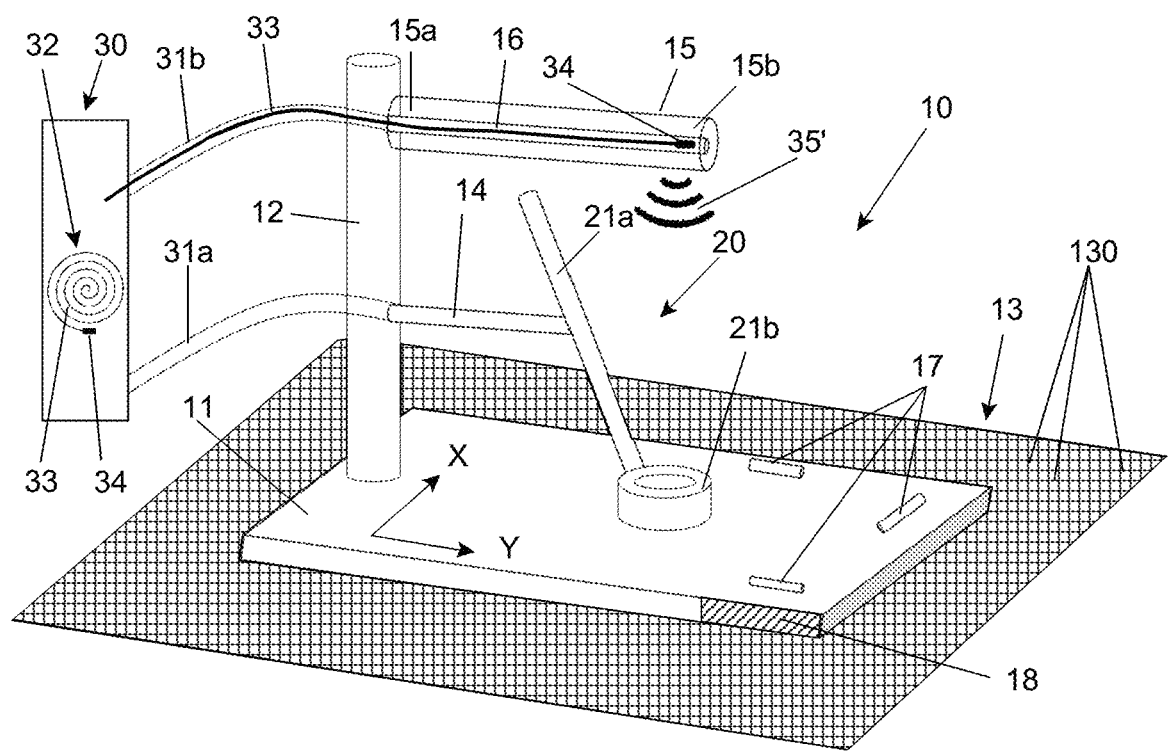
FIG. 4b the device of FIG. 1b in a first test condition.
Figure 4C:
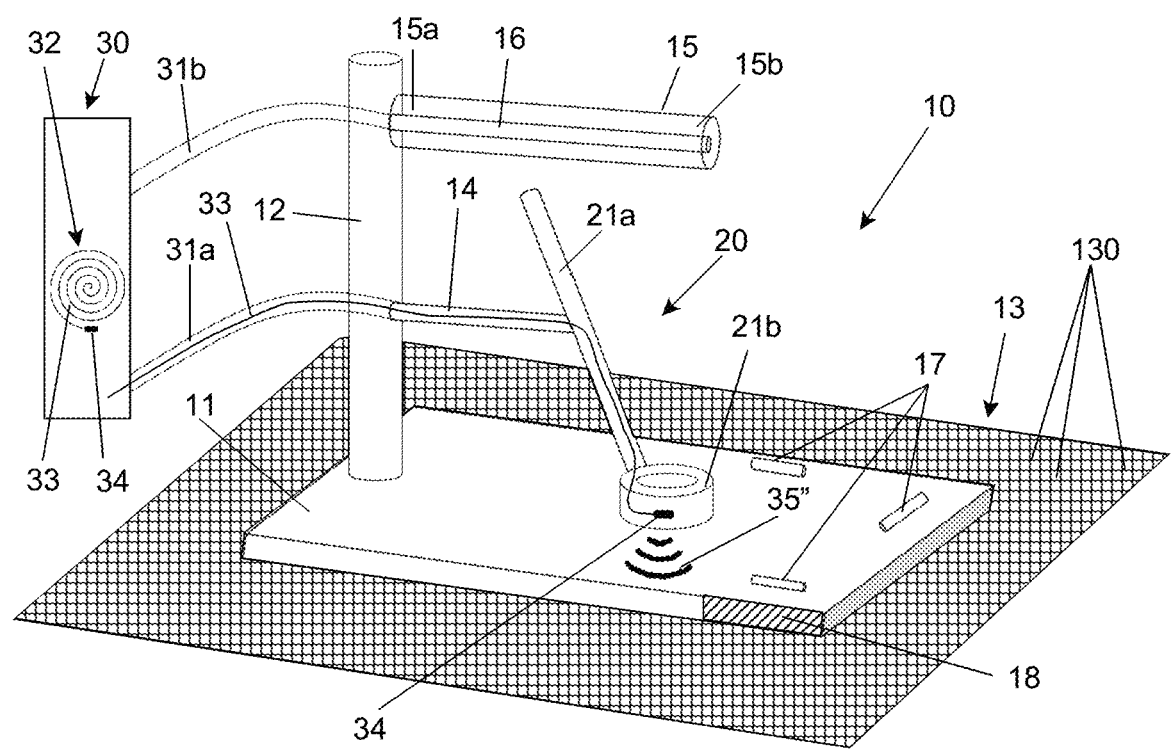
FIG. 4c the device of FIG. 1b in a second test condition.

The radiation capturing screen 13 is capable of capturing radiation impinging on the surface of radiation capturing screen 13 and converting said radiation into an electric signal, which signal can be outputted or read out from the screen using suitable image processing means, schematically depicted with reference numeral 18 (FIGS. 4a-4c). In particular the radiation capturing screen 13 is composed of an array of plurality of radiation capturing pixel elements or radiation pixel sensors 130. When reading out all the radiation capturing sensors 130 at any given time, one independent image of the radiation impinging on radiation capturing screen 13 can be obtained. As such, the radiation capturing screen 13 is capable of capturing radiation being emitted by a radiation emitting source and converting said radiation in subsequent, independent images, which images are read out for further processing.

For clarification in the FIGS. 1a and 1b (but also in the other FIGS. 3, and 4a-c the orthogonal dimensions of the radiation capturing screen 13/test supporting device 10 are properly denoted with X and Y. Said orthogonal dimensions X and Y are conformal to the X and Y orientations in the images being captured by the radiation capturing screen 13 as depicted in FIGS. 5a-5d, 6 and 8a-8d.

Figure 2:
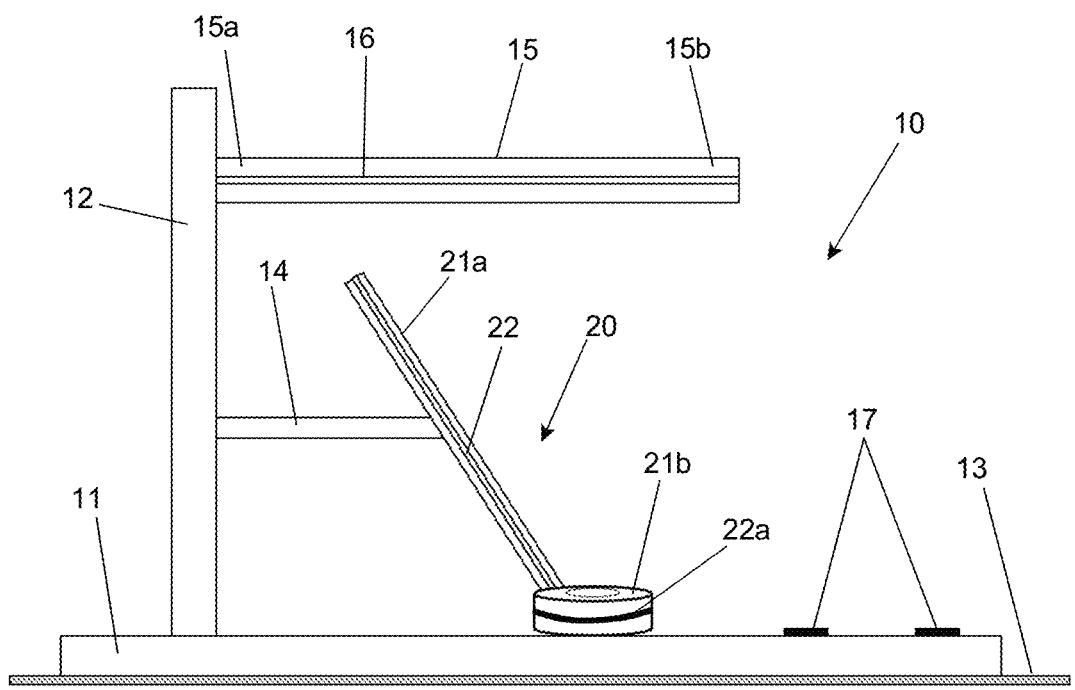
FIG. 2 a side view of the example of FIG. 1b provided with a brachytherapy application to be tested being held by the device.

In FIG. 2 a setup of the test supporting device 10 is depicted with a brachytherapy applicator 20 being held by the applicator test holder 14. The brachytherapy applicator 20 is here denoted as a brachytherapy ring applicator used for performing high dose rate genealogical radiation treatments.

However, it is observed that the test supporting device 10 can also be used for testing other types of brachytherapy applicators, such as vaginal, rectal or breast applicator probes, which are to be inserted into the vagina or the rectum, or a surgical breast cavity of a human or animal body.

In this embodiment, the brachytherapy ring applicator is composed of an applicator shaft 21a and an ring applicator 21b. Preferably, the brachytherapy applicator 20 to be tested is provided with at least one applicator channel, denoted in FIG. 2 and further in the description with reference numeral 22. The applicator channel 22 is provided in the applicator shaft 21a and extends in longitudinal direction through the elongated applicator shaft 21a towards the ring applicator 21b, from where the applicator channel 22 continues in a circular applicator channel 22a (see also FIG. 6).

Figure 3:
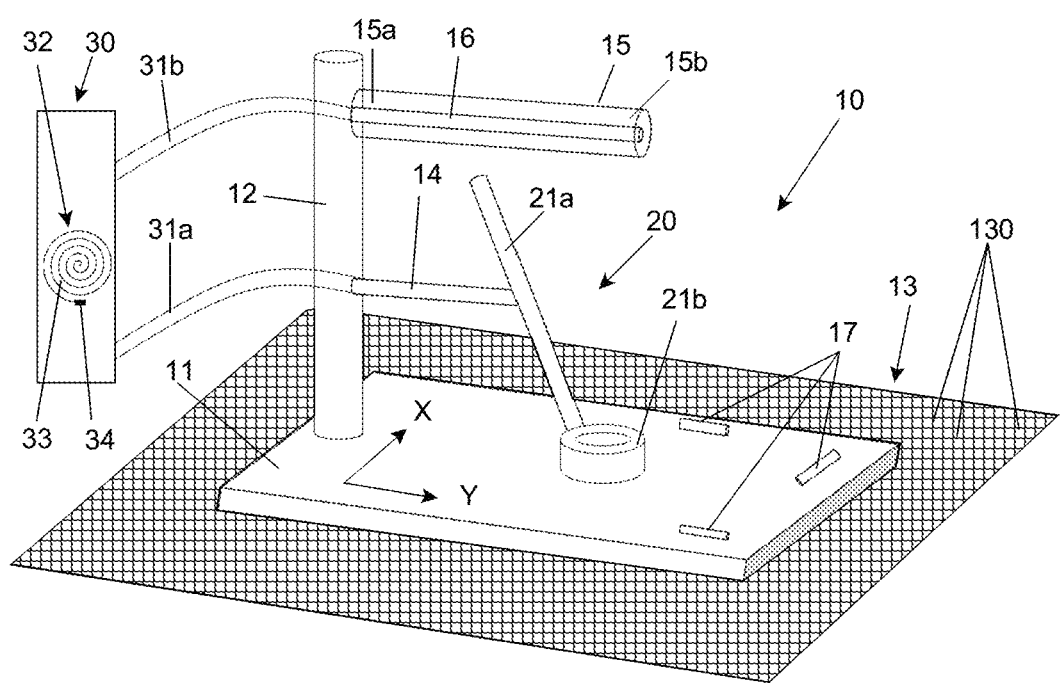
FIG. 3 another view of the example of FIG. 1b provided with a brachytherapy application to be tested being held by the device as well as source drive means.

FIG. 3 depicts another example of the test supporting device 10 under testing conditions, having a brachytherapy applicator 20 (here again the brachytherapy ring applicator), being held by the applicator test holder test holder 14.

As shown in FIG. 2, but also in the subsequent FIGS. 3, 4b and 4c, the brachytherapy ring applicator 20 is being held by the applicator test holder 14 in such manner that the applicator shaft 21a is connected or clamped to the applicator test holder test holder 14, whereas the ring applicator 21b is positioned just above the support plate 11 and the radiation capturing screen 13.

In FIG. 3 reference numeral 30 denotes radiation emitting source drive means, which consists of a radiation shielded compartment 32, which contains a source wire 33, that is wound up in the form of a spool. The free end of source wire 33 is provided with a radiation emitting source 34.

The radiation emitting source 34 is preferably a high dose rate or a pulsed dose rate radiation emitting source. A typical HDR-type radiation emitting source is for example an $^{192}$Ir (Iridium) source, which emits radiation following the principle of natural radioactive decay. Such $^{192}$Ir sources are suitable for performing brachytherapy radiation treatments.

The radiation emitting source drive means 30 can be coupled to the test supporting device 10 and in particular with both the imaging holder 15 and the applicator test holder 14 using suitable first and second source guide channels 31a and 31b. The radiation emitting source drive means 30 can also be part of an afterloading apparatus or even constitute the afterloading apparatus.

FIG. 4a discloses the test supporting device 10 according to the invention in an initial working condition. As shown, the radiation emitting source drive means 30 are coupled with the test supporting device 10 via a first source guide channel 31a, which connects the radiation emitting source drive means 30 and in particular the radiation shielded compartment 32, which contains the spool of source wire 33 and the radiation emitting source 34, with the applicator test holder 14.

Similarly, a second source guide channel 31b is provided connecting the radiation emitting source drive means 30, in particular the radiation shielded compartment 32 with the imaging holder channel 16 provided in the imaging holder 15. In FIG. 4b the radiation emitting source 34 is indicated in this position.

In the initial working condition as depicted in FIG. 4a, a radiation emitting source 34 is guided from the radiation emitting source drive means 30/radiation shielded compartment 32 through the second source guide channel 31b and the imaging holder channel 16, until the end of said imaging holder channel 16 near or at the distal imaging holder 15b. The guidance of the radiation emitting source 34 is accomplished by a suitable unwinding of the spool of the source wire 33 with the radiation emitting source 34 connected to the distal end of said source wire 33. By unwinding the spool of the source wire 33 the radiation emitting source 34 is pushed out of the radiation shielded compartment 32, through the second source guide channel 31b and into the imaging holder channel 16 towards the distal imaging holder end 15b.

As the radiation emitting source 34 is preferably a continuously emitting HDR source, for example $^{192}$Ir, the radiation being emitted (denoted with reference numeral 35 in FIG. 4a) is collected and captured by the radiation capturing screen 13 in one or more subsequent, independent images, which images are classified as 'initial images' or 'images of an initial type' or 'images of an initial view'. The radiation 35 being captured by the multiple radiation pixel sensors 130 is converted by the radiation pixel sensors 130 in an electronic signal, which electronic signals are inputted to the imaging processing means 18. The image processing means 18 process said converted electronic signal into an image that can be visualized on a suitable viewing screen for diagnosis by the testing personnel.

In the FIGS. 4a-4c the image processing means 18 are depicted as being an integral part of the test supporting device 10. In another embodiment the image processing means 18 can be incorporated in a separate unit, which unit is coupled with the radiation capturing screen 13. In that example the radiation capturing screen 13 outputs the radiation-to-electronic converted signals from the multiple radiation pixel sensors 130 via a suitable signal cable to the unit containing the image processing means 18. The image processing means 18 can be implemented as a personal computer with the image processing being run as a computer program.

Figure 5:
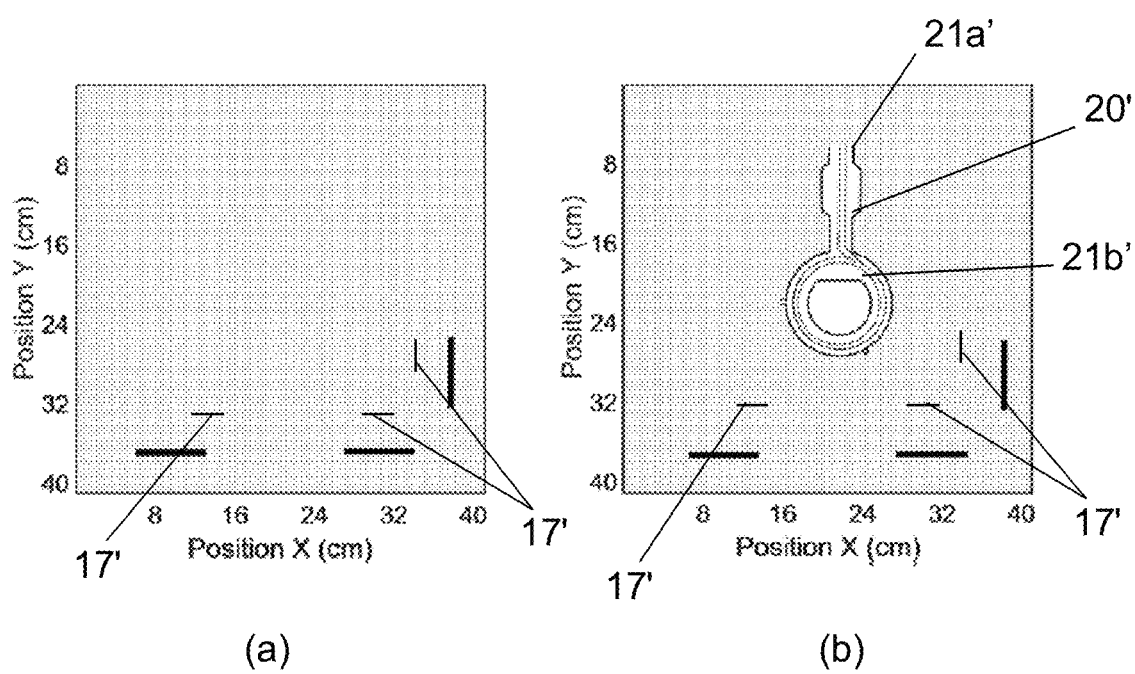
Figure 5:
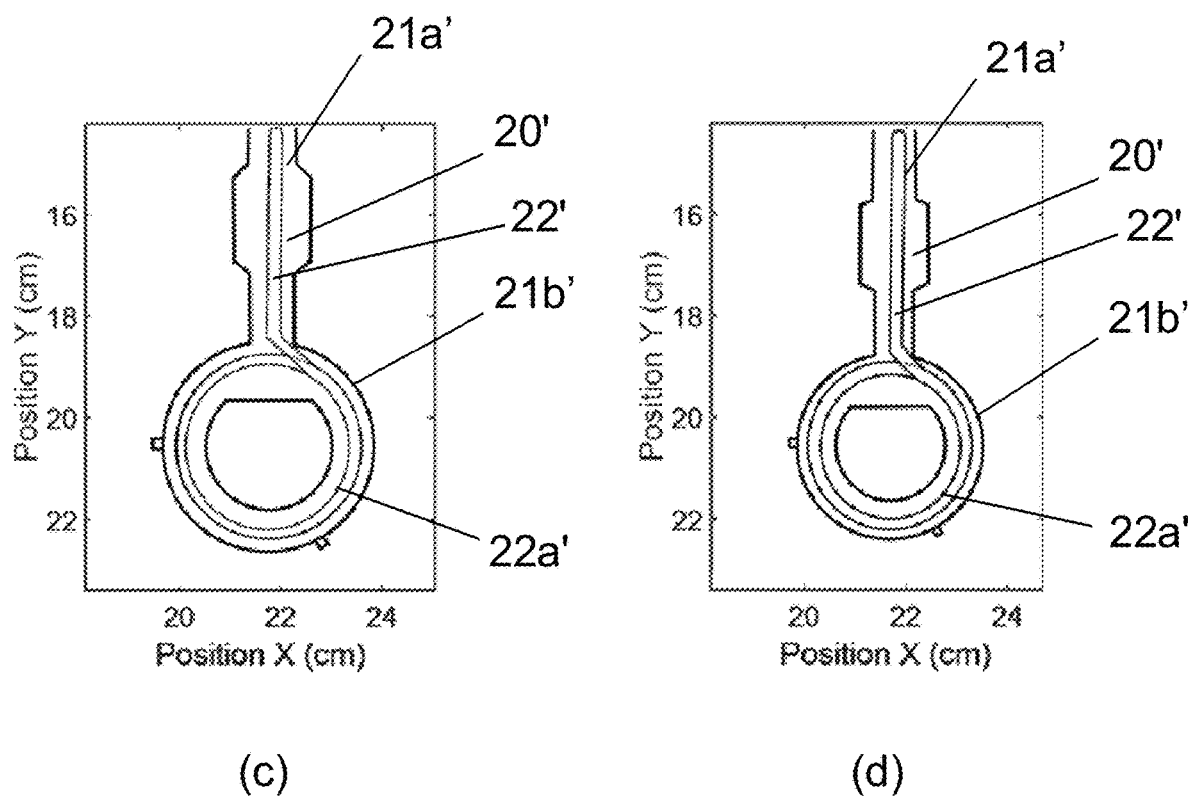

An example of an initial image (or image of the initial view) is depicted in FIG. 5a, which FIG. 5a depicts the bare exposure of the radiation capturing screen 13 to the radiation emitting source 34 contained in the imaging holder 15, with no brachytherapy applicator 20 to be tested being held by the applicator test holder 14. FIG. 5a as such depicts an image of an initial view only depicting the image shadows 17' conformal to the radio opaque or fiducial position markers 17 present on the surface of the support plate 11. In particular, the initial testing condition as depicted in FIG. 4a merely serves for calibrating the radiation capturing screen 13 for background exposure and/or for pixel sensitivity differences during the subsequent testing of the brachytherapy applicator 20. This background exposure is also needed to identify dead pixels in the radiation capturing screen 13, and to correct for them in subsequent use of the device and the method, in particular when processing the several types of images for visualizing and quantifying the brachytherapy applicator.

The exposure of the radiation capturing screen 13 in the initial testing condition as depicted in FIG. 4a results after processing by the image processing means 18 in one or more subsequent, independent images of an initial type or view. Said images of the initial type are used for calibration and background subtraction of the images obtained with the radiation capturing screen 13 during the subsequent testing conditions, whilst testing the brachytherapy applicator 20 using the test supporting device 10 according to the invention.

Subsequent to the initial working condition as depicted in FIG. 4a, FIG. 4b depicts a next (first) testing condition of the test supporting device according to the invention, wherein a brachytherapy applicator 20 is being held by the applicator test holder 14. Also in this example the brachytherapy applicator 20 to be tested is constructed as a brachytherapy ring applicator.

It is noted that the first testing phase of the test supporting device 10 using the testing method according to the invention can also be performed without performing the initial testing phase or step as depicted in FIG. 4a. The initial testing step is not necessary for testing purposes according to the method according to the invention using the test support device 10. Obviating the initial testing step for calibrating the radiation capturing screen 13 for background exposure and/or for pixel sensitivity differences is possible in the event, that the radiation capturing screen 13 has already been calibrated.

In case the initial calibration/testing step as shown in FIG. 4a has been performed the radiation emitting source 34 is to be retracted from the imaging holder channel 16 back into the radiation shielded compartment 32 from the source drive means 30. This to prevent unnecessary health risks for the personnel operating the test supporting device 10. After retraction of the radiation emitting source 34 back into the source drive means 30, a brachytherapy applicator 20 to be tested can be mounted to the applicator test holder 14 by the testing personnel.

Similar as to the initial testing condition as depicted in FIG. 4a also in this (first) testing condition the same radiation emitting source 34 is being guided through the second source guide channel 41b and the imaging holder channel 16 towards the same distal end position in the source channel 16 near or at the distal imaging holder end 15b as in the initial working position depicted in FIG. 4a.

Radiation being emitted by the radiation emitting source 34 at its distal position in the imaging holder channel 16 of the imaging holder 15 is emitted in the direction of the radiation capturing screen 13, and also exposes the brachytherapy ring applicator 20 being positioned between the radiation capturing screen 13 and the imaging holder 15. Said radiation, in FIG. 4b denoted with 35', is captured by the radiation capturing screen 13, converted into suitable electronic signals by the plurality of radiation pixel sensors 130 and inputted to the image processing means 18. After processing by the image processing means 18 subsequent, independent images are outputted. These images, being classified as 'first images' or 'images of a first type' or 'images of a first view', also contain an image shadow of the brachytherapy applicator 20 to be tested.

These subsequent, independent images of the first view being obtained from the radiation 35' being captured by the radiation capturing screen 13 contain and depicts the outer contour or outer dimensions and other details, such as one or more applicator channels of the brachytherapy applicator 20 under test. FIG. 5b depicts such an image of the first view/type, being captured by the radiation capturing screen 13, with a brachytherapy ring applicator 20 being held by the applicator test holder 14 and being exposed by radiation 35' being emitted by the radiation emitting source 34 being positioned in the imaging holder 15.

Next to the shadows 17' of the position markers 17 also the shadow contour 20' of the brachytherapy applicator 20 is shown. The image of FIG. 5b also depicts the shadow of the applicator shaft 21a (depicted with 21a' in the image) as well as the source channel in the ring applicator 21b, which is depicted with reference numeral 21b' in the image of FIG. 5b.

FIG. 4c depicts the test supporting device 10 in a second testing condition (or testing position) wherein the radiation emitting source 34 is guided through the first source guide channel 31a and through the applicator test holder 14 and the applicator channel 22 towards the ring applicator 21b' of the brachytherapy applicator 20.

To this end, similar as the imaging holder 15, the applicator test holder 14 is provided with an applicator test holder channel (not depicted), which test holder channel is provided as a bore running through the elongated shaft-like applicator test holder 14 from the proximal applicator test holder end (being attached with the support stand 12) till the free, distal applicator test holder end. The first source guide channel 31a is to be connected with this applicator test holder channel. The pathway of the holder channel subsequently will continue in the applicator channel 22.

Yet in another example the first source guide channel 31a is directed connected with the free end of the applicator shaft 21a, such that the pathway of the first source guide channel 31a continues directly in the applicator channel 22.

In both testing configurations the radiation emitting source 34 is guided and advanced (or even pushed) from the radiation shielded compartment 32 into the first source guide channel 31a with the source (guide) wire 33, and ultimately into the applicator channel 22 towards the ring-shaped ring applicator channel 22a. Similarly to the testing conditions as depicted in FIGS. 4a and 4b also in this testing condition of FIG. 4c the radiation emitting source 34 will continuously emit radiation, now denoted with 35", which is captured by the plurality of radiation pixel sensors 130 of the radiation capturing screen 13. After conversion into suitable electronic signals by the plurality of radiation pixel sensors 130, these electronic signals are inputted to the image processing means 18 and after processing outputted as subsequent, independent images, which images are classified as 'images of a second view' or 'images of a second type'.

Figure 4D:
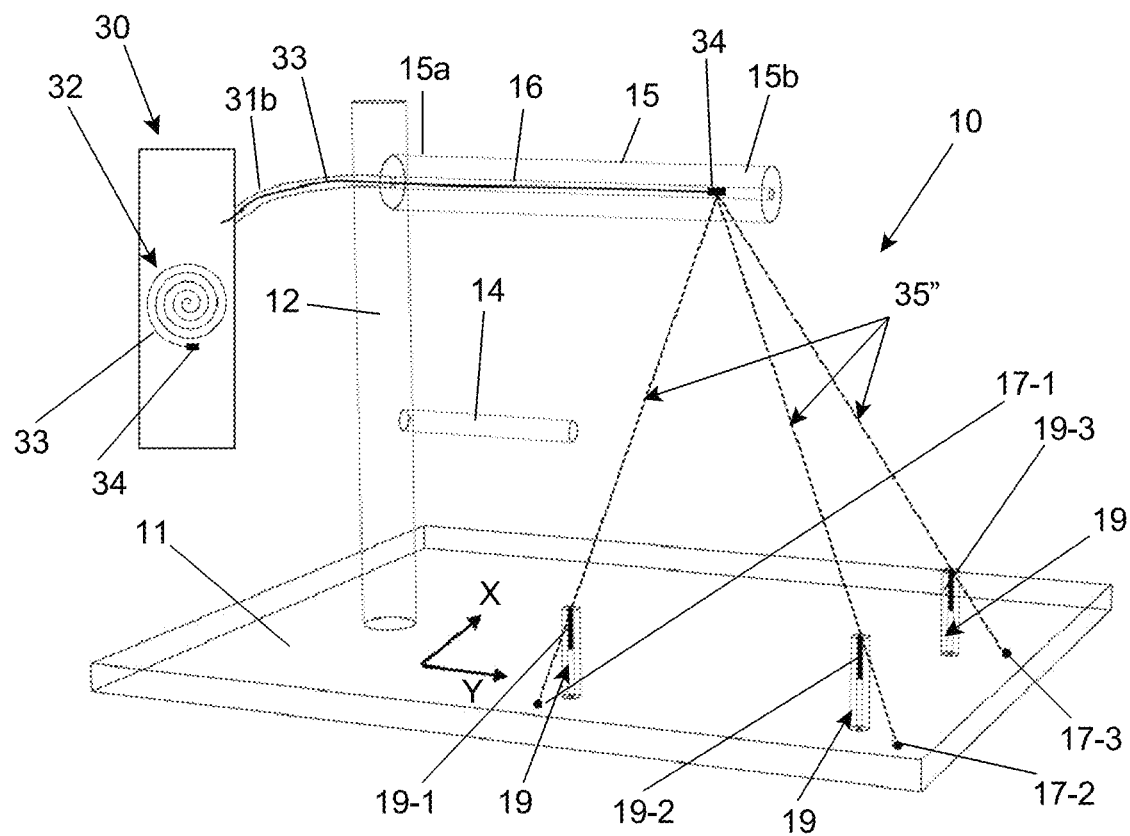
FIG. 4d another example of the device of FIG. 1b in an initial test condition.

FIG. 4d depicts another example of a device 10 according to the invention, being used in an initial working condition more or less identical as depicted in FIG. 4a. For the sake of clarity, in FIG. 4d, the radiation capturing screen 13 consisting of the multiple radiation pixel sensors 130 for capturing the radiation 35 being captured by the radiation emitting source 34 and for converting the radiation pixel sensors 130 in an electronic signal, is being omitted for clarity purposes.

In a similar fashion as with the description of the initial working condition of FIG. 4a, a radiation emitting source 34 is guided from the radiation emitting source drive means 30/radiation shielded compartment 32 through the second source guide channel 31b and the imaging holder channel 16, until the end of said imaging holder channel 16 near or at the distal imaging holder 15b. The guidance of the radiation emitting source 34 is accomplished in a similar manner by a suitable unwinding of the spool of the source wire 33 with the radiation emitting source 34 connected to the distal end of said source wire 33. By unwinding the spool of the source wire 33 the radiation emitting source 34 is pushed out of the radiation shielded compartment 32, through the second source guide channel 31b and into the imaging holder channel 16 towards the distal imaging holder end 15b.

The radiation emitting source 34 is preferably a continuously emitting HDR source, for example $^{192}$Ir, the radiation being emitted (denoted with reference numeral 35 in FIG. 4d) is collected and captured by the (non-depicted) radiation capturing screen 13 in one or more subsequent, independent images, which images are classified as 'initial images' or 'images of an initial type' or 'images of an initial view'. The radiation 35 being captured by the multiple radiation pixel sensors 130 is converted by the radiation pixel sensors 130 in an electronic signal, which electronic signals are inputted to the imaging processing means 18. The image processing means 18 process said converted electronic signal into an image that can be visualized on a suitable viewing screen for diagnosis by the testing personnel.

The initial testing condition as depicted in FIG. 4a merely serves for calibrating the radiation capturing screen 13 for background exposure and/or for pixel sensitivity differences during the subsequent testing of the brachytherapy applicator 20. This background exposure is also needed to identify dead pixels in the radiation capturing screen 13, and to correct for them in subsequent use of the device and the method, in particular when processing the several types of images for visualizing and quantifying the brachytherapy applicator. This is explained in connection with FIGS. 5a-5d.

In the embodiment of FIG. 4d the surface of the support plate 11 is provided with similar radio opaque or fiducial position markers 17-1; ... 17-3 which will create image shadows 17' in the subsequent 'images of an initial view'. Additionally the support plate 11 is provided with support markers 19, the number of which correspond with the number of position markers 17-1, 17-2, 17-3. Each support marker 19 is positioned near each corresponding position marker 17-1, 17-2, 17-3. Each support marker 19 is constituted as an bar or element pointing upwards (perpendicular to the surface of the support plate 11) in the direction towards the distal imaging holder 15b, and each free end of the upwards pointing support marker 19 is provided with radio opaque or fiducial projection markers 19-1; 19-2; 19-3.

When calibrating the device herewith it is also possible to calibrate the exact position of the radiation emitting source 34 at the end of said imaging holder channel 16 near or at the distal imaging holder 15b. The radiation emitting source 34 will be properly positioned at the end of said imaging holder channel 16 near or at the distal imaging holder 15b for calibrating purposes, if both the radio opaque or fiducial projection markers 19-1; 19-2; 19-3 and the corresponding position marker 17-1, 17-2, 17-3 exactly overlap each in the subsequent 'images of an initial view' being obtained. If the 'images of an initial view' depict a blurry or distorted image, that is a non-overlapping or incorrect overlap image of both markers 19-1; 19-2; 19-3 and 17-1, 17-2, 17-3, it is concluded that the radiation emitting source 34 is incorrectly positioned at the final end of said imaging holder channel 16 near or at the distal imaging holder 15b.

If a fully correct overlapping image of both markers 19-1; 19-2; 19-3 and 17-1, 17-2, 17-3 is shown in the 'images of an initial view' it is concluded that the radiation emitting source 34 is correctly positioned at the final end of said imaging holder channel 16 near or at the distal imaging holder 15b.

Figure 6:
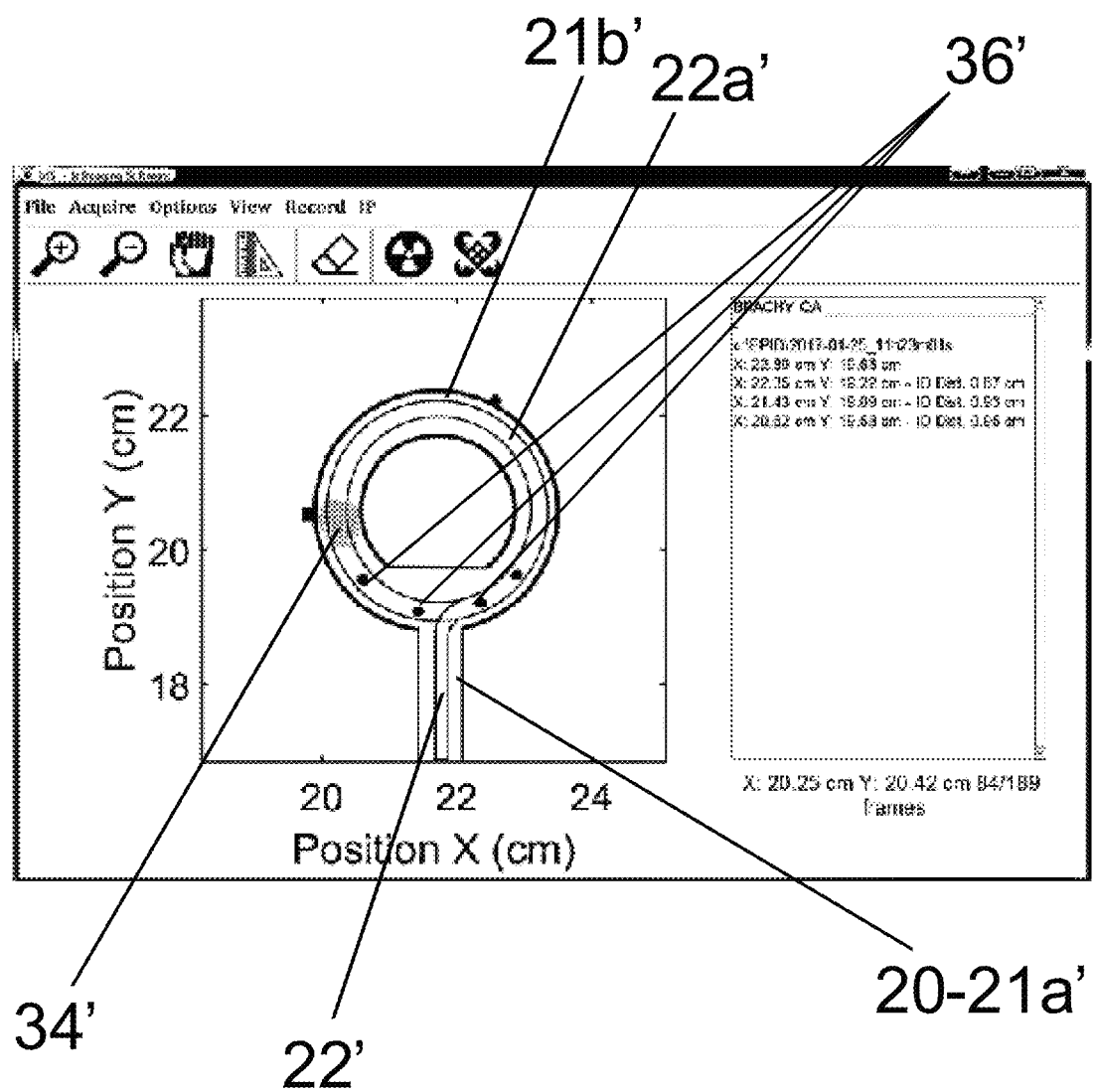
FIG. 6 an image in accordance with the image shown in FIG. 5d, now with a source wire and radiation emitting source, the brachytherapy applicator being in the second test condition shown in FIG. 4c.

An example of such an image of the second view/type is depicted in FIG. 6. In this FIG. 6 an image is shown of partly the applicator shaft 21a (in the image depicted with reference numeral 21a') of the brachytherapy ring applicator 20 (20' in the image). Also the ring applicator 21b (21b' in the image) is clearly visible, as well as the applicator channel 22 (22' in the image) and the ring-shaped applicator channel 22a (2a' in the image). Also clearly visible is the position of the radiation emitting source 34 (34' in FIG. 6) present in the ring applicator channel 22a'.

Herewith it is possible to visualize and quantify the geometrical dimensions of the brachytherapy applicator 20 during test based on the processing by the image processing means 18 of the subsequent, independent images being captured, in particular based on the images of the first type being captured in the first working condition of the test supporting device 10 as shown in FIG. 4b (as well as in FIG. 5b) and the independent images of the second type being captured with the test supporting device 10 as shown in the second working/test condition as depicted in FIG. 4c and the image as depicted in FIG. 6.

Said visualizing and quantifying of the geometrical dimensions of the brachytherapy applicator 20 based on the independent images of the first and second type being captured can be further improved by correcting the subsequent, independent images of the first and seconds type as depicted in FIGS. 5b and 6 with the subsequent, independent images of the initial type, as obtained with the test supporting device 10 positioned in the initial test condition as depicted in FIG. 4a (and its corresponding image as obtained and depicted in FIG. 5a).

The subsequent, independent images of the first and second type with the subsequent, independent images of the initial type, are subtracted to remove the effect of the double exposure of the capturing screen 13. Also any pixel sensitivity differences of the plurality of radiation pixel sensor elements 130 are compensated for. Thereby the remaining subtracted image only contains useful information on the geometry of the applicator (FIG. 5c-d). Said correction is being performed by the image processing means 18 and is based on the subtraction of the intensity values of the several pixel sensors 130 in an image of the first and/or second type from the intensity values of the corresponding pixel sensors 130 in an image of the initial type.

The result of such an corrected image is depicted in FIG. 5c. All pixel intensity values of the image of the initial view/type are corrected by the image processing means 18 with the intensity values of the corresponding pixel sensors 130 in an image of the initial type.

A further correction by the image processing means 18 of the images of the first and second type pertains to the correction for the point source effect, which results in high-intensity regions right below the radiation emitting source 34 due to the higher exposure of the radiation sensor elements 130 compared with the decreasing exposure of radiation sensor elements 130 away from the exposure point directly below the radiation emitting source 34 towards the edges of the radiation capturing screen 13.

The effect of correcting the subsequent, independent images of the first and second type, as for example depicted in FIG. 5b is shown in FIGS. 5c and 5d. FIG. 5c shows the projection of the brachytherapy applicator 20 (20' in the image) being corrected for the background exposure of the radiation capturing screen radiation capturing screen 13, which background exposure is obtained with the initial test condition of the test supporting device as shown in FIG. 4a, with the image of the initial type thus obtained being depicted in FIG. 5a.

FIG. 5d depicts the image of FIG. 5c after a further process step performed by the image processing means 18, wherein the image of the brachytherapy applicator 20' of FIG. 5c is corrected for any deformation due to the projection of the brachytherapy applicator 20 on the surface of the radiation capturing screen 13 and the fact that the radiation emitting source 34 is considered being a point source. This deformation is depicted in FIG. 7, showing the radiation emitting source 34 as well as the brachytherapy applicator 20 positioned at a distance h' respectively h above the radiation capturing screen 13.

Figure 7:
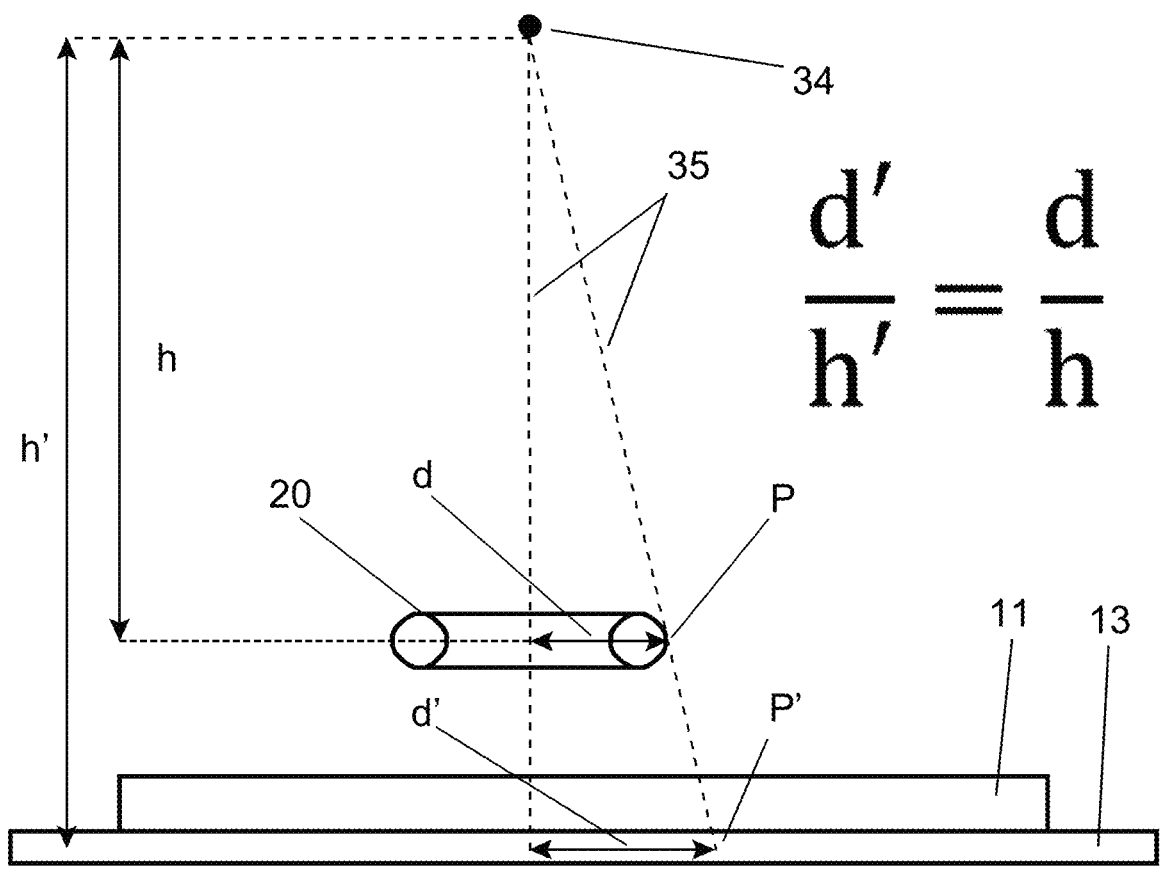
FIG. 7 the correction process for correcting projected distortion.

In FIG. 7 an arbitrary point P of the brachytherapy applicator 20 is represented in the image as being captured by the radiation capturing screen 13 with reference denotation P'. The distance d' between the projected P' and the projected position of the radiation emitting source 34 at the level of the radiation capturing screen 13 is larger than the distance d between the actual arbitrary point P of the brachytherapy applicator 20 and the projected source position of the radiation emitting source 34 at the level of the brachytherapy applicator 20 itself.

This effect of deformation due to the projection of the brachytherapy applicator 20 in the image as being captured by the radiation capturing screen 13 is being corrected by the image processing means 18 using the relation:

$$\frac{d'}{h'} = \frac{d}{h}$$

With this relation, the image processing means 18 are arranged in correcting any distorted displacement of the brachytherapy applicator 20 in the images being obtained with the radiation capturing screen 13. In particular, the image processing means 18 are arranged in repeating the correction step for each pixel seen in the X- and Y-direction of the image based on the relationship as above and as depicted in FIG. 7, as long as the projected heights h and h' are known.

In particular by using the method steps of the invention the image processing means 18 are arranged in correcting (or converting) any point identified with the orthogonal coordinates (X', Y') in an uncorrected image of the first and/or second view/type as depicted in FIG. 5b and/or 5c into a corrected or converted point (X, Y) depicting the actual dimension within the image with the relationships:

$$X = X' * \frac{h}{h'} \text{ and } Y = Y' * \frac{h}{h'}$$

If necessary, the linear interpolation between the pixels in the X- and/or Y-direction are being applied. The correction by using the method steps of the invention and performed by the image processing means 18 results in a corrected image of the brachytherapy applicator 20 (20' in the image) as shown in FIG. 5d depicting the actual dimensions of the brachytherapy applicator 20 being held by the applicator test holder 14. It is observed that both FIG. 5c and FIG. 5d are at the same scale, but that the corrected shadow 20' in FIG. 5d is smaller than the shadow 20' in FIG. 5c (in fact smaller by a correction factor defined by h (the distance between the source 34 and the applicator 20) divided by the height h' (the distance between the source 34 and the radiation capturing screen 13), hence $$\text{correction factor} = \frac{h}{h'}$$

Figure 8:
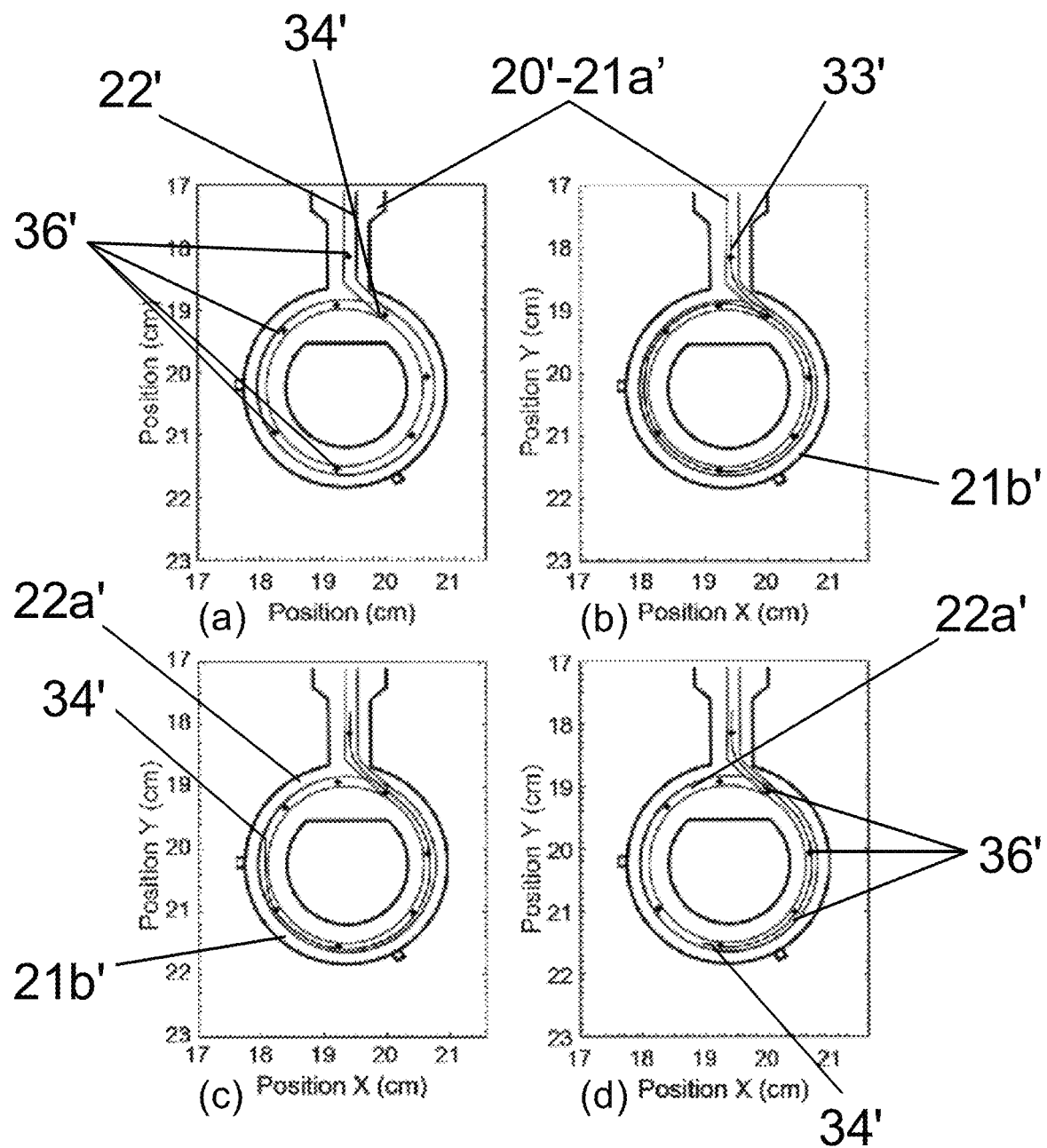
FIGS. 8a-8d further images of a brachytherapy applicator containing a source wire and radiation emitting source at several dwell positions.

FIGS. 8a-8b disclose several images obtained with the radiation capturing screen 13 of the brachytherapy ring applicator 20-21a-21b (20'-21a'-21b' in the images). In particular FIGS. 8a till 8d disclose the inner geometrical dimensions of the brachytherapy applicator 20' being properly visualized and quantified using the test supporting device 10 and the method according to the invention. In FIG. 8a multiple dwell positions 36' are depicted at which the radiation emitting source 34 has been positioned using the source guide wire 33 through the applicator channel 22 and 22a.

According to the image processing technique implemented by the image processing means 18 are arranged in determining the positions (denoted as dwell positions 36') of the radiation emitting source 34 in at least three subsequent, independent images of the second type being captured. Based on the at least three determined positions 36' the image processing means 18 decide whether said positions 36' fall within a predefined distance range (for example a distance range of 0.3-0.7 mm).

Once the image processing means 18 have decided that said individual (here three) positions 36' are within said predefined distance range, the image processing means 18 identify that the radiation emitting source 34 is positioned at a dwell position 36' within the brachytherapy applicator 20.

In a further, additional method step, which step can be performed additionally but not necessarily always following the dwell position identification steps described above, the image processing means 18 are arranged in verifying that the radiation emitting source 34 in fact remains at the dwell position 36' being identified for a predefined dwell time. Said predefined dwell time can for example be determined by the frame rate at which frame rate the radiation capturing screen together with the image processing means 18 outputs the subsequent, independent images. For example in case the frame rate is equal to 7 (or 5) fps, meaning a frame acquisition requires 0.14 s (0.2 s) a dwell time of 0.43 s (or 0.6 s) is being defined for three subsequent, independent images and if the radiation emitting source 34' is being identified at the same position in said three subsequent, independent images then said dwell time is properly identified and verified. This procedure can be repeated for all dwell source positions and this allows verifying all dwell times accurately. This allows a proper and accurate treatment plan to be generated with the correct dwell positions and dwell times as identified with the brachytherapy applicator under test.

With the device 10 according to the invention the testing of the geometrical dimensions (both external and internal of a brachytherapy applicator) can be properly tested and visualized and quantified prior to the use of said brachytherapy applicator 20 for use in a real brachytherapy radiation treatment. As shown in FIG. 8a-8b-8c-8d, the inner contour of the applicator channel 22-22a can be properly visualized and quantified and any deviation from the manufacturers' specification can be detected; in particular, any conformance with the manufacturers' specifications can be properly verified with the test supporting device and the test method according to the invention.

In particular, the subsequent images obtained during the initial test condition, the first test condition and the second test condition as depicted in FIGS. 4a-4b-4c allow for a proper mechanical inspection of the brachytherapy application as to its outer dimensions as such brachytherapy applicator is often inserted into a cavity of the human or animal body under treatment. Also, any deviations such as offsets or even defects in for example the configuration or contour of the one or more applicator channels present in the brachytherapy applicator under test, can be readily observed.

Any deviation from the manufacturers' specifications can be taken into account when using the tested brachytherapy applicator in a radiation treatment dose planning system. In particular, the radiation treatment dose planning system can be inputted with the updated applicator dimensions as obtained during testing, allowing the radiation treatment dose planning system to prepare correct treatment plans using the correct dimensions and configuration of the brachytherapy applicator used for performing the radiation treatment.

With the device and the method according to the invention, each brachytherapy applicator can be tested at regular intervals between brachytherapy radiation treatments, thereby observing significant deviations from the manufacturers' specifications or applicator dimensions previously obtained during previous tests, for example due to mishandling and/or damage during past radiation treatments.

LISTING OF REFERENCE NUMERALS 10 test supporting device
11 support plate
12 support stand
13 radiation capturing screen
130 radiation capturing elements
14 test holder
15 imaging holder
15a proximal imaging holder end
15b distal imaging holder end
16 imaging holder channel
17 (17-1; . . . ; 17-3) visual markers (17' when captured in image)
18 image processing means
19 support markers
19-1; . . . ; 19-3 projection markers
20 brachytherapy applicator (20' when captured in image)
21a applicator shaft (21a' when captured in image)
21b ring applicator (21b' when captured in image)
22 applicator channel (22' when captured in image)
22a ring applicator channel (22a' when captured in image)
30 radiation emitting source drive means/afterloading apparatus
31a first source guide channel
31b second source guide channel
32 radiation shielded compartment containing spool of source wire and radiation emitting source
33 source wire (33' when captured in image)
34 radiation emitting source (34' when captured in image)
35 radiation emitted for initial view
35' radiation emitted for first view
35" radiation emitted for second view
36' (virtual) dwell positions in applicator channel 22/22'

The invention claimed is:

1. A method for testing of a brachytherapy applicator prior to using the brachytherapy applicator in high dose rate or pulse dose rate brachytherapy radiation treatments, said method comprising the steps of:
providing a testing device including a radiation capturing screen, an imaging holder positioned at a distance from the radiation capturing screen and being arranged for accommodating a high dose rate or pulsed dose rate brachytherapy radiation emitting source in a first test condition, and an applicator test holder positioned between the imaging holder and the radiation capturing screen, the applicator test holder being arranged for holding the brachytherapy applicator under test,
  wherein the radiation capturing screen is arranged in said first test condition in capturing radiation being emitted by said high dose rate or pulsed dose rate brachytherapy radiation emitting source in subsequent, independent images of a first type,
  wherein in said first test condition the imaging holder accommodates the high dose rate or pulsed dose rate brachytherapy radiation emitting source and the applicator test holder holds the brachytherapy applicator under test,
  wherein the radiation capturing screen is arranged in a second test condition in capturing radiation being emitted by said high dose rate or pulsed dose rate brachytherapy radiation emitting source in subsequent, independent images of a second type,
  wherein in said second test condition the applicator test holder holds the brachytherapy applicator under test, and the brachytherapy applicator under test holds the high dose rate or pulsed dose rate brachytherapy radiation emitting source,
c) positioning a brachytherapy applicator to be tested in the applicator test holder of the testing device;
d) positioning in a first test condition a high dose rate or pulsed dose rate brachytherapy radiation emitting source in the imaging holder of the testing device;
e) capturing radiation being emitted by said high dose rate or pulsed dose rate brachytherapy radiation emitting source with said radiation capturing screen in subsequent, independent images of a first type;
f) positioning in a second test condition the high dose rate or pulsed dose rate brachytherapy radiation emitting source in the brachytherapy applicator to be tested and being held in the applicator test holder;
g) capturing radiation being emitted by said radiation emitting source with said radiation capturing screen in subsequent, independent images of a second type; and
h) visualizing and quantifying geometrical dimensions of said brachytherapy applicator based on processing the subsequent, independent images of the first and second type being captured during said first and second test conditions.

2. The method according to claim 1, wherein step f) comprises the step of:
f-1) positioning the high dose rate or pulsed dose rate brachytherapy radiation emitting source for certain dwell times at one or more dwell positions in the brachytherapy applicator.

3. The method according to claim 2, further comprising the steps of:
i-1) determining the positions of the high dose rate or pulsed dose rate brachytherapy radiation emitting source in at least three subsequent, independent images being captured during step f-1);
i-2) deciding whether said positions are within a predefined distance range; and
i-3) when it has been decided that said positions are within said predefined distance range, identifying that the high dose rate or pulsed dose rate brachytherapy radiation emitting source is positioned at a dwell position within the brachytherapy applicator, and
i-4) verifying that the high dose rate or pulsed dose rate brachytherapy radiation emitting source remains at the dwell position being identified for a predefined dwell time.

4. The method according to claim 1, wherein step c) is preceded by the steps of:
a) positioning in an initial test position the high dose rate or pulsed dose rate brachytherapy radiation emitting source in the imaging holder of the testing device with no brachytherapy applicator to be tested being held in the applicator test holder;
b) capturing radiation being emitted by said high dose rate or pulsed dose rate brachytherapy radiation emitting source with said radiation capturing screen in subsequent, independent images of an initial type.

5. The method according to claim 4, wherein step h) comprises the step of:

h-1) correcting the subsequent, independent images of the first and second type for background exposure signals using the subsequent, independent images of the initial type.

6. The method according to claim 1, further comprising the steps of:
   j-1) generating applicator dimension data relating to the geometrical dimensions of said brachytherapy applicator being visualized and quantified;
   j-2) inputting said applicator dimension data in a radiation treatment planning system.

7. A testing device for testing a brachytherapy applicator prior to using the brachytherapy applicator in high dose rate or pulsed dose rate brachytherapy radiation treatments, said testing device comprising:
   a radiation capturing screen;
   an imaging holder positioned at a distance from the radiation capturing screen and being arranged for accommodating a high dose rate or pulsed dose rate brachytherapy radiation emitting source in a first test condition;
   an applicator test holder positioned between the imaging holder and the radiation capturing screen, the applicator test holder being arranged for holding the brachytherapy applicator under test,
   wherein the radiation capturing screen is arranged in said first test condition in capturing radiation being emitted by said high dose rate or pulsed dose rate brachytherapy radiation emitting source in subsequent, independent images of a first type,
   wherein in said first test condition the imaging holder accommodates the high dose rate or pulsed dose rate brachytherapy radiation emitting source and the applicator test holder holds the brachytherapy applicator under test, and
   wherein the radiation capturing screen is arranged in a second test condition in capturing radiation being emitted by said high dose rate or pulsed dose rate brachytherapy radiation emitting source in subsequent, independent images of a second type,
   wherein in said second test condition the applicator test holder holds the brachytherapy applicator under test, and the brachytherapy applicator under test holds the high dose rate or pulsed dose rate brachytherapy radiation emitting source,
   wherein the radiation capturing screen is arranged for capturing radiation being emitted by said high dose rate or pulsed dose rate brachytherapy radiation emitting source in subsequent, independent images in an initial test condition, wherein the imaging holder accommodates the high dose rate or pulsed dose rate brachytherapy radiation emitting source and the applicator test holder holds no brachytherapy applicator under test.

8. A testing device for testing a brachytherapy applicator prior to using the brachytherapy applicator in high dose rate or pulsed dose rate brachytherapy radiation treatments, said testing device comprising:
   a radiation capturing screen;
   an imaging holder positioned at a distance from the radiation capturing screen and being arranged for accommodating a high dose rate or pulsed dose rate brachytherapy radiation emitting source in a first test condition;
   an applicator test holder positioned between the imaging holder and the radiation capturing screen, the applicator test holder being arranged for holding the brachytherapy applicator under test,
   wherein the radiation capturing screen is arranged in said first test condition in capturing radiation being emitted by said high dose rate or pulsed dose rate brachytherapy radiation emitting source in subsequent, independent images of a first type,
   wherein in said first test condition the imaging holder accommodates the high dose rate or pulsed dose rate brachytherapy radiation emitting source and the applicator test holder holds the brachytherapy applicator under test, and
   wherein the radiation capturing screen is arranged in a second test condition in capturing radiation being emitted by said high dose rate or pulsed dose rate brachytherapy radiation emitting source in subsequent, independent images of a second type,
   wherein in said second test condition the applicator test holder holds the brachytherapy applicator under test, and the brachytherapy applicator under test holds the high dose rate or pulsed dose rate brachytherapy radiation emitting source,
   wherein the testing device comprises radiation emitting source drive means arranged for driving in said first test condition said high dose rate or pulsed dose rate brachytherapy radiation emitting source through said imaging holder,
   wherein the radiation capturing screen is arranged for capturing radiation being emitted by said high dose rate or pulsed dose rate brachytherapy radiation emitting source in subsequent, independent images in an initial test condition, wherein the imaging holder accommodates the high dose rate or pulsed dose rate brachytherapy radiation emitting source and the applicator test holder holds no brachytherapy applicator under test.

9. The testing device according to claim 8, wherein said radiation emitting source drive means is further arranged for driving in said second test condition said radiation emitting source through said brachytherapy applicator, being held by said applicator test holder, and
   wherein the radiation capturing screen is arranged for capturing radiation being emitted by said high dose rate or pulsed dose rate brachytherapy radiation emitting source in subsequent, independent images in an initial test condition, wherein the imaging holder accommodates the high dose rate or pulsed dose rate brachytherapy radiation emitting source and the applicator test holder holds no brachytherapy applicator under test.

10. The testing device according to claim 8, wherein said radiation emitting source drive means is connected to an afterloading apparatus, and
    wherein the radiation capturing screen is arranged for capturing radiation being emitted by said high dose rate or pulsed dose rate brachytherapy radiation emitting source in subsequent, independent images in an initial test condition, wherein the imaging holder accommodates the high dose rate or pulsed dose rate brachytherapy radiation emitting source and the applicator test holder holds no brachytherapy applicator under test.

* * * * *